(12) United States Patent
Kim

(10) Patent No.: US 10,864,332 B2
(45) Date of Patent: Dec. 15, 2020

(54) GUIDE DEVICE FOR INJECTION NEEDLE PUNCTURE

(71) Applicants: AMOLIFESCIENCE CO., LTD., Seoul (KR); Ji Hoon Kim, Seoul (KR)

(72) Inventor: Ji Hoon Kim, Seoul (KR)

(73) Assignees: AMOLIFESCIENCE CO., LTD., Seoul (KR); Ji Hoon Kim, Seoul (KR)

(*) Notice: Subject to any disclaimer, the term of this patent is extended or adjusted under 35 U.S.C. 154(b) by 821 days.

(21) Appl. No.: 15/541,002

(22) PCT Filed: Dec. 21, 2015

(86) PCT No.: PCT/KR2015/014016
§ 371 (c)(1),
(2) Date: Jun. 29, 2017

(87) PCT Pub. No.: WO2016/108485
PCT Pub. Date: Jul. 7, 2016

(65) Prior Publication Data
US 2017/0361032 A1  Dec. 21, 2017

(30) Foreign Application Priority Data
Dec. 31, 2014 (KR) .......... 10-2014-0195629

(51) Int. Cl.
*A61M 5/42* (2006.01)
*A61B 8/08* (2006.01)

(52) U.S. Cl.
CPC .............. *A61M 5/427* (2013.01); *A61M 5/42* (2013.01); *A61B 8/0841* (2013.01)

(58) Field of Classification Search
CPC ........ A61M 5/427; A61M 5/42; A61B 8/0841
See application file for complete search history.

(56) References Cited

U.S. PATENT DOCUMENTS 4,108,165 A * 8/1978 Kopp .................. A61B 8/0833
600/461
4,899,756 A    2/1990 Sonek
(Continued)

FOREIGN PATENT DOCUMENTS

JP  2005-192915 A  7/2005
JP  2012-081134 A  4/2012
(Continued)

OTHER PUBLICATIONS

ISA/KR, International Search Report dated Apr. 26, 2016 in International Application No. PCT/KR2015/014016, total p. 4 with English translation.
(Continued)

*Primary Examiner* — Theodore J Stigell
*Assistant Examiner* — Sean A Frith
(74) *Attorney, Agent, or Firm* — Masuvalley & Partners

(57) ABSTRACT

Provided is a guide device for injection needle puncture. The guide device for needle puncture according to one embodiment of the present invention comprises: a body; a guide part which has a guide hole provided therein so as to be tilted at a certain angle along the height direction, the guide hole allowing an injection needle to pass therethrough so that during injection needle puncture, the insertion angle of the injection needle can be constantly maintained; and a sliding member which is coupled to the body so as to be slidingly movable, wherein the spaced distance between the guide hole and a medical ultrasound apparatus is adjusted through relative movement of the body or the sliding member so that a target location into which the distal end of the injection needle is inserted can be located on entrance path of the injection needle.

17 Claims, 9 Drawing Sheets

(56) References Cited

U.S. PATENT DOCUMENTS

| | | | |
|---|---|---|---|
| 5,941,889 A * | 8/1999 | Cermak | A61B 8/0833 606/130 |
| 2002/0133079 A1 | 9/2002 | Sandhu | |
| 2003/0212414 A1 | 11/2003 | Sonek | |
| 2003/0230870 A1 * | 12/2003 | Sabol | A63C 10/18 280/618 |
| 2006/0020211 A1 * | 1/2006 | Tokumoto | A61B 8/4209 600/464 |
| 2010/0010505 A1 | 1/2010 | Herlihy et al. | |
| 2012/0330159 A1 * | 12/2012 | Orome | A61B 5/15003 600/461 |
| 2013/0261553 A1 * | 10/2013 | Sheldon | A61M 25/0113 604/117 |
| 2014/0034800 A1 * | 2/2014 | Strong | A61B 8/12 248/229.1 |
| 2014/0249504 A1 * | 9/2014 | Franklin | A61M 25/06 604/507 |
| 2014/0276081 A1 * | 9/2014 | Tegels | A61B 8/085 600/461 |
| 2014/0343406 A1 * | 11/2014 | Damjanovic | A61M 5/427 600/424 |

FOREIGN PATENT DOCUMENTS

| | | | |
|---|---|---|---|
| KR | 20-2000-0005148 U | 3/2000 | |
| WO | 95/02663 A2 | 1/1995 | |
| WO | WO-9502663 A2 * | 1/1995 | A61B 17/3403 |

OTHER PUBLICATIONS

UK Office Action dated May 22, 2020 for Application No. GB1710207.0, 4 pages.

* cited by examiner

GUIDE DEVICE FOR INJECTION NEEDLE PUNCTURE

RELATED APPLICATIONS

This application is the U.S. National Phase application under 35 U.S.C. § 371 of International Patent Application No. PCT/KR2015/014016, International Filing Date Dec. 21, 2015, entitled Guide Device For Injection Needle Puncture; which claims priority to Korean Patent Application No. KR10-2014-0195629 filed on Dec. 31, 2014, which are hereby expressly incorporated by reference in their entirety for all purposes.

TECHNICAL FIELD

The present invention relates to an auxiliary device for a medical ultrasound apparatus, and more particularly, to a guide device for injection needle puncture that guides an insertion angle of an injection needle so that precise treatment is possible even by an unskilled person.

BACKGROUND ART

Generally, attenuation of ultrasound waves occur according to density and thickness in a biological tissue, and the shape of an inside of the human body is imaged and checked using the attenuation. Treatment under ultrasound induction in which not only a site of lesion is checked using a medical ultrasound apparatus but treatment such as pain relieving is performed by directly injecting chemicals into the site of lesion or vein and relieving inflammation and edema is frequently performed.

However, in a generally used medical ultrasound apparatus (1), because the shape of an inside of the human body is two-dimensionally imaged in a direction perpendicular to that in which ultrasound waves are transmitted, it is difficult for a needle to be inserted into a precise position by distinguishing adjacent vein and artery.

When, as illustrated in FIG. 1, an end of an injection needle (10) is not inserted into a precise position (T) and is inserted into another position (T') which is not a desired position (e.g., vein), precision of treatment is decreased, and repetitive puncturing is required to insert the injection needle into the desired position.

Further, when an injection needle is punctured into an erroneous position and perforation occurs in artery, a serious problem in which a patient's life is at risk due to excessive bleeding may occur, or perforation and pain occur in an unnecessary site.

This has problems such as unnecessary damage to a patient and reoperation due to imprecise treatment. Particularly, in a case of an unskilled person, the possibility of the above-described risks are extremely high.

DISCLOSURE

Technical Problem

The present invention has been devised in consideration of the above aspects, and an objective of the present invention is to provide a guide device for injection needle puncture that allows an injection needle to always be precisely inserted at the same insertion angle when the injection needle is inserted into skin of the human body so that a target position can be placed on a path of the injection needle.

Another objective of the present invention is to provide a guide device for injection needle puncture that adjusts an angle of a guide hole configured to guide an insertion angle of an injection needle punctured into the human body so that a position into which the injection needle is punctured can be variously adjusted.

Technical Solution

To solve the above problem, the present invention provides a guide device for injection needle puncture that includes a body; a guide part that has a guide hole provided therein to be tilted at a certain angle along a height direction, the guide hole allowing an injection needle to pass therethrough so that, when the injection needle is punctured into the human body, an insertion angle of the insertion needle is guided and the insertion angle is constantly maintained; and a sliding member slidably coupled to the body, wherein a separation distance between a medical ultrasound apparatus and the guide hole is adjusted so that a target position into which an end of the injection needle is to be inserted can be located on an entry path of the injection needle by relative movement of the body or the sliding member.

A partial length of the guide hole including an upper end exposed to the outside may be formed to have a cross-sectional area that is relatively larger than a remaining portion so that insertion of the injection needle into the guide hole is facilitated.

A cross-sectional area of the guide hole may gradually decrease from top to bottom at least partially or entirely so that insertion of the injection needle into the guide hole is facilitated.

A scales part may be included to check the separation distance between the medical ultrasound apparatus and the guide hole.

Here, the scales part may have the form of a ruler disposed along a longitudinal direction at one surface of the sliding member or may have the form of a ruler disposed along a longitudinal direction at one surface of the body.

An indicator configured to indicate a position corresponding to a lower end of the guide hole may be disposed at one side of the body.

The guide hole may be formed to penetrate the body along the height direction of the body.

The guide part may be coupled to be rotatable with respect to the body to adjust an angle of the guide hole.

The guide part may include a guide main body rotating about a hinge shaft with respect to the body, and the guide hole may be formed to penetrate the guide main body along a height direction of the guide main body.

A lever part may be provided at one end of the hinge shaft.

An angle indicating part may be provided at one side of the body to check an angle of rotation of the guide main body.

A plurality of angle adjustment grooves that are concentrically arranged about the hinge shaft may be provided at one side of the guide main body, and a fixing pin that is inserted through a side portion of the body may be inserted into the angle adjustment grooves to fix the angle of rotation of the guide main body.

A spring member may be provided at one end side of the fixing pin to press the fixing pin in one direction.

The separation distance between the guide hole and the medical ultrasound apparatus may be a linear distance between the lower end of the guide hole and a lower end of the medical ultrasound apparatus.

An angle of inclination of the guide hole may be formed to be an angle in the range of 0° to 90° with respect to a horizontal surface. Preferably, the angle of inclination of the guide hole may be formed to be any one angle of 30°, 45°, or 60° with respect to the horizontal surface and may be 45°, more preferably.

A contact part coming into contact with one surface of the medical ultrasound apparatus may be provided at a free end side of the sliding member.

The contact part may be a plate-shaped member perpendicularly extending from an end of the sliding member toward one side.

A fixing member for fixing to the medical ultrasound apparatus may be provided at the contact part.

The fixing member may be a hollow frame part to surround a perimeter of the medical ultrasound apparatus.

The frame part may be detachably coupled to the contact part.

A stopper member configured to restrict movement of the sliding member may be provided in the body.

The stopper member may be at least one set screw that is screw-coupled to one side of the body, and when the set screw moves by rotation, an end of the set screw may press the sliding member at the middle of the length thereof.

Advantageous Effects

According to the present invention, when an injection needle is inserted into a guide hole that is set at a certain angle, because an injection needle is always inserted at the same insertion angle when the injection needle is inserted into skin of the human body, a target position is placed on a path of the injection needle, and precision of treatment can be increased even by an unskilled person.

Further, because a position into which an injection needle, is punctured can be variously adjusted by adjusting an angle of a guide hole configured to guide an insertion angle of the injection needle which is punctured into the human body, convenience in use can be improved.

DESCRIPTION OF DRAWINGS

FIG. 6A illustrates a case in which the guide hole is formed to have the same cross-sectional area throughout its entire length, FIG. 6B illustrates a case in which the guide hole is formed to have a cross-sectional area that gradually decreases from top to bottom along a part of its entire length, and FIG. 6C illustrates a case in which the guide hole is formed to have a cross-sectional area that gradually decreases from top to bottom throughout its entire length.

MODES OF THE INVENTION

Figure 1:
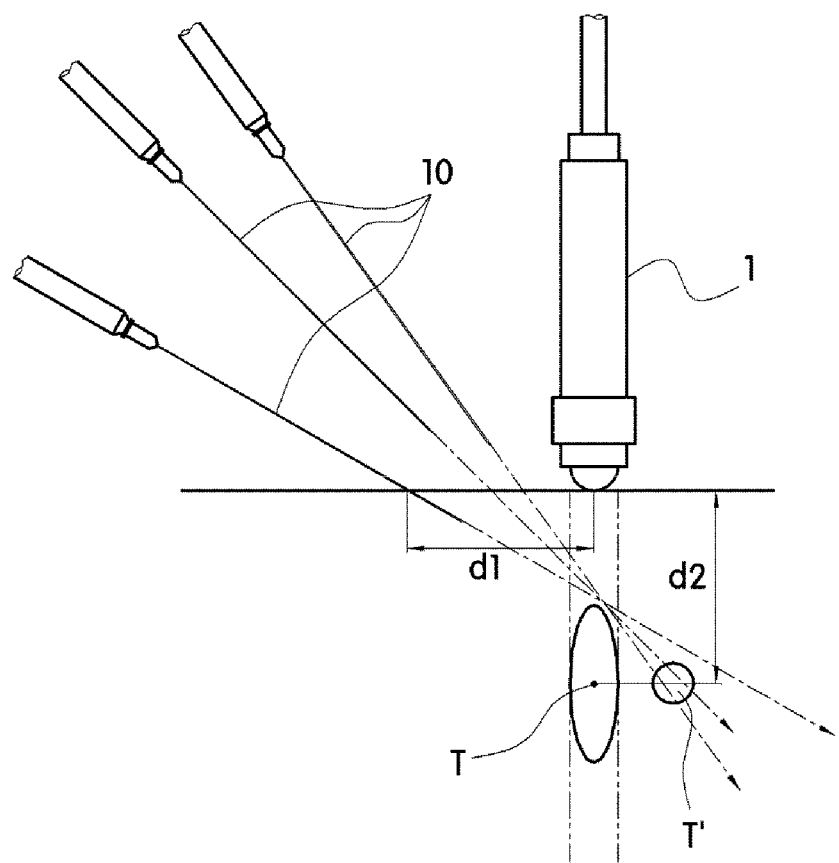
FIG. 1 is a conceptual diagram illustrating a difference from a target point due to an insertion angle of an injection needle when the injection needle is generally punctured.

Hereinafter, embodiments of the present invention will be described in detail with reference to the accompanying drawings so that one of ordinary skill in the art to which the present invention pertains can easily practice the embodiments. The present invention can be implemented in various different forms and is not limited to embodiments described herein. Parts unrelated to the description are omitted from the drawings to clearly describe the present invention, and like reference numerals will be assigned to like or similar elements throughout.

Figure 5:
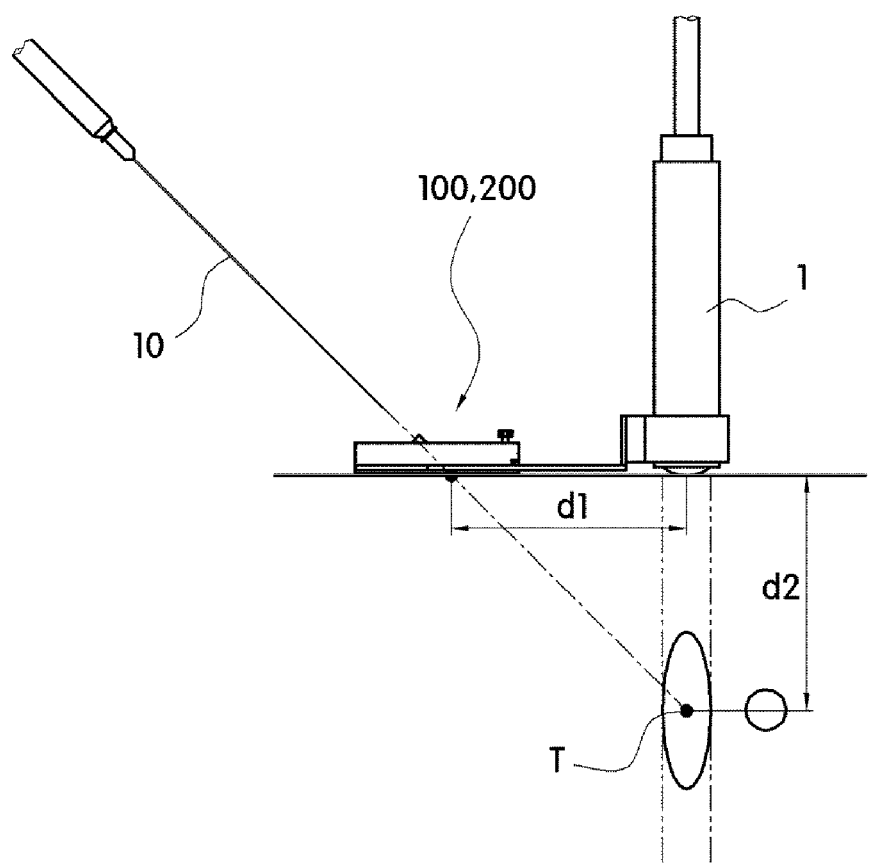
FIG. 5 is a use state diagram of the guide device for injection needle puncture according to an embodiment of the present invention.

First, referring to FIG. 5, guide devices for injection needle puncture 100 and 200 according to an embodiment of the present invention are for allowing an end of an injection needle 10 to be precisely inserted into a desired position (e.g., vein) in the human body by using a screen that is imaged by a medical ultrasound apparatus.

That is, in a process in which the injection needle 10 is inserted into the human body, the injection needle 10 can be moved along a desired path by an insertion angle of the injection needle 10 being guided so that the injection needle 10 can always be inserted at the same angle into skin of the human body.

Here, the insertion angle of the injection needle 10 is set by a depth d2 from skin of the human body to a target position that is measured by ultrasound waves and a distance from the medical ultrasound apparatus to a position into which the injection needle 10 will be inserted using a length of a side of a right-angled triangle.

Because the depth d2 from the skin of the human body to the target position that is measured by ultrasound waves can be easily measured using a medical ultrasound apparatus 1, in a case in which the insertion angle of the injection needle 10 is set, an end of the injection needle 10 can be inserted into a precise position along a set path when the distance from the medical ultrasound apparatus to the position into which the injection needle 10 will be inserted is varied.

For example, in a case in which the insertion angle of the injection needle 10 is set as 45°, when the injection needle 10 is inserted into a position at which the separation distance (the distance from the medical ultrasound apparatus to the position into which the injection needle 10 will be inserted) is the same as the depth d2 from the skin of the human body to the target position, which is measured using ultrasound waves, a desired target position T is placed collinear with an entry path of the injection needle 10, and precise treatment can be performed.

This is because, in a case of a right-angled isosceles triangle with an internal angle of 45°, the lengths of the base and the height are the same except that of the hypotenuse.

Here, although the insertion angle of the injection needle 10 is 45° in the above example, it should be noted that the insertion angle is not limited thereto and may be variously set within an angle range larger than 0° and smaller than 90°.

Also, the insertion angle of the injection needle 10 is used as the same meaning as a set angle of a guide hole 122 that will be described below.

As described above, the guide devices for injection needle puncture 100 and 200 that guide the entry path of the injection needle 10 to allow an operator to perform precise treatment include bodies 110 and 210, guide parts 120 and 220, and a sliding member 130.

By sliding by moving relative to the sliding member 130, the bodies 110 and 210 allow a distance from the medical ultrasound apparatus 1 to be adjusted.

For this, the bodies 110 and 210 have at least one groove part 112 formed by being cut away along the longitudinal direction, and linear sliding movement of the sliding member 130 is guided by the groove part 112 by the sliding member 130 being inserted into the groove part 112.

Here, although the groove part configured to guide movement of the sliding member 130 is illustrated and described as having the shape of a groove with one open side and being disposed at one side of the body, it should be noted that embodiments are not limited thereto, and the groove may also have the shape of a closed groove into which the sliding member 130 is completely inserted.

In this case, at least one stopper member is provided at one side of the bodies 110 and 210 so that linear movement relative to the sliding member 130 can be restricted. The stopper member may be at least one set screw 114 that is screw-coupled to the side of the bodies 110 and 210.

By this, when the set screw 114 moves by rotation, an end of the set screw 114 presses the sliding member 130 at the middle of the length thereof, and movement relative to the sliding member 130 is restricted.

In the process in which the separation distance between the guide hole 122 and the medical ultrasound apparatus 1 is set and then the injection needle 10 is inserted into the guide hole 122, the set screw 114 restricts movement of the bodies 110 and 210 or the sliding member 130 relative to each other to prevent the separation distance between the guide hole 122 and the medical ultrasound apparatus 1 from being changed.

Here, the separation distance between the guide hole 122 and the medical ultrasound apparatus 1 may be a distance between a probe provided in the medical ultrasound apparatus 1 and the guide hole 122, and more specifically, signifies a linear distance between a lower end of the guide hole 122 and the probe of the medical ultrasound apparatus 1.

The guide parts 120 and 220 are for guiding the insertion angle of the injection needle 10 and always constantly maintaining the insertion angle of the injection needle 10 when the injection needle 10 is punctured into the human body.

For this, the guide hole 122 through which the injection needle 10 passes is formed to penetrate the guide parts 120 and 220.

In this case, the guide hole 122 is formed to be gradually inclined upward from the lower end with respect to the horizontal surface at least partially. Due to this, when the injection needle 10 is inserted into the guide hole 122, the insertion angle of the injection needle 10 which is inserted into the human body is guided and always constantly maintained by the guide hole 122.

For example, the guide hole 122 may be formed at an angle between 0° to 90°, preferably, at an angle of 30°, 45°, or 60°, and more preferably, at an angle of 45°.

Figure 4:
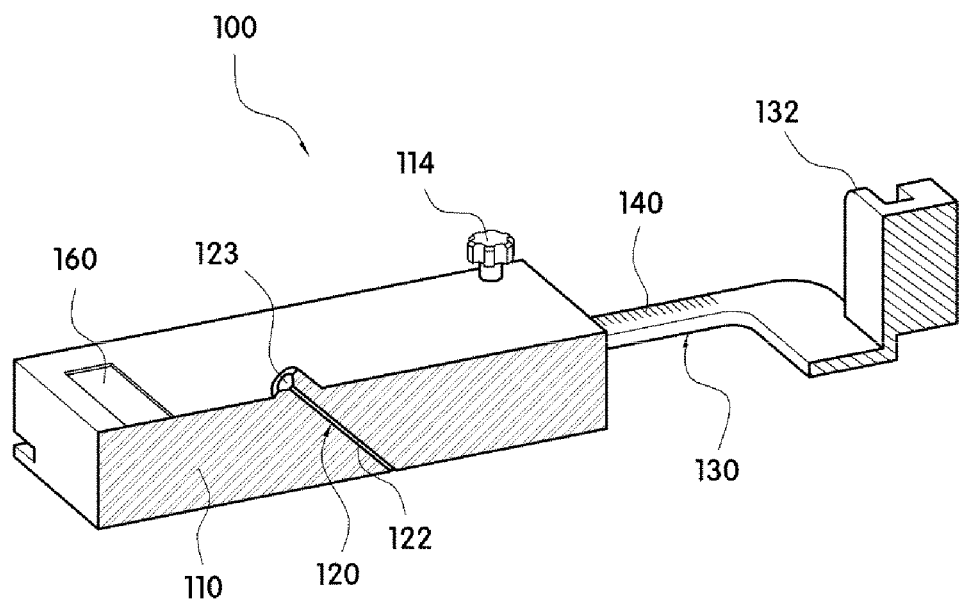
FIG. 4 is a partially cut-away view of FIG. 2.
Figure 10:
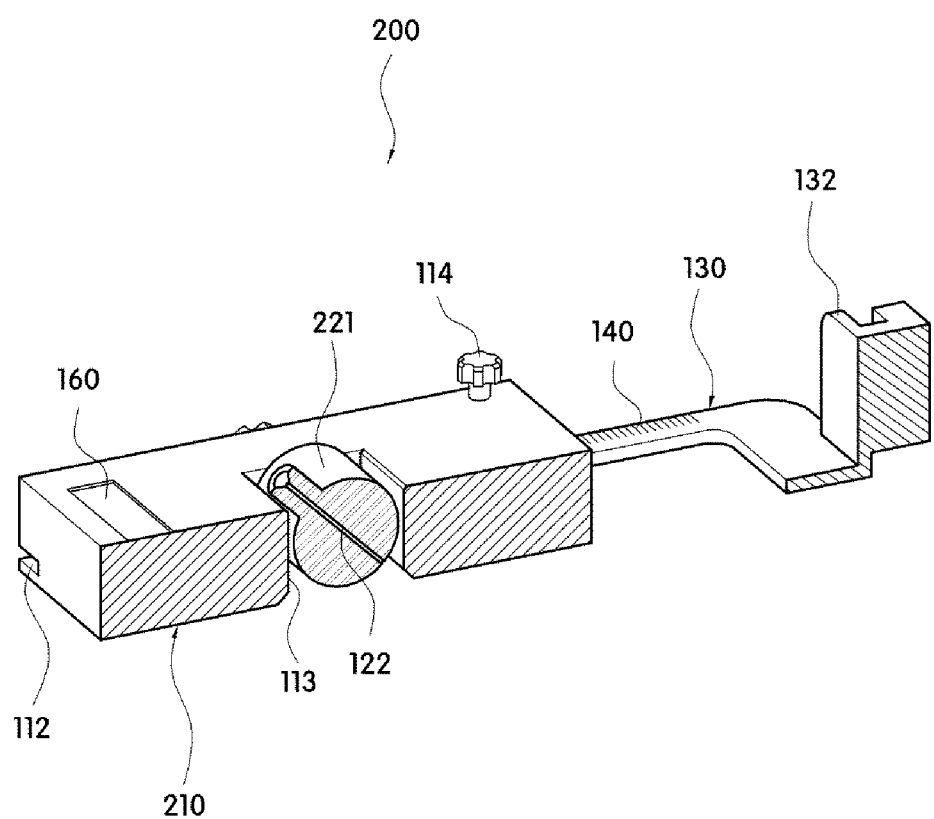
FIG. 10 is a partially cut-away view taken along line A-A in FIG. 7.

In this case, as illustrated in FIGS. 4 and 10, the guide hole 122 may include an enlarged opening part 123 having a relatively large cross-sectional area formed at an upper side so that the injection needle 10 can easily enter the guide hole 122. Here, the enlarged opening part 123 refers to a partial length, which includes an upper end exposed to the outside, of an entire length of the guide hole 122.

Figure 6A:
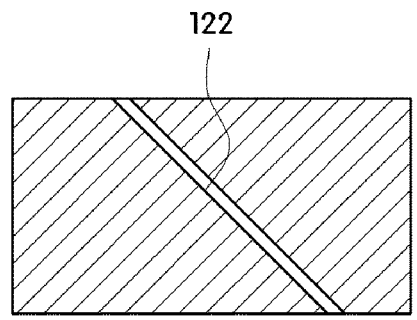
FIGS. 6A to 6C are schematic views illustrating various shapes of a guide hole in the guide device for injection needle puncture according to an embodiment of the present invention, where
Figure 6B:
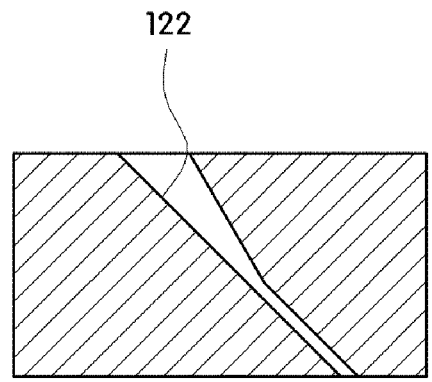
Figure 6C:
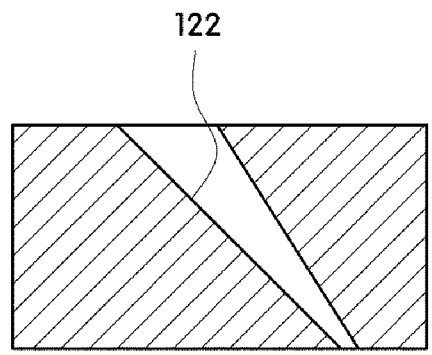
Figure 7:
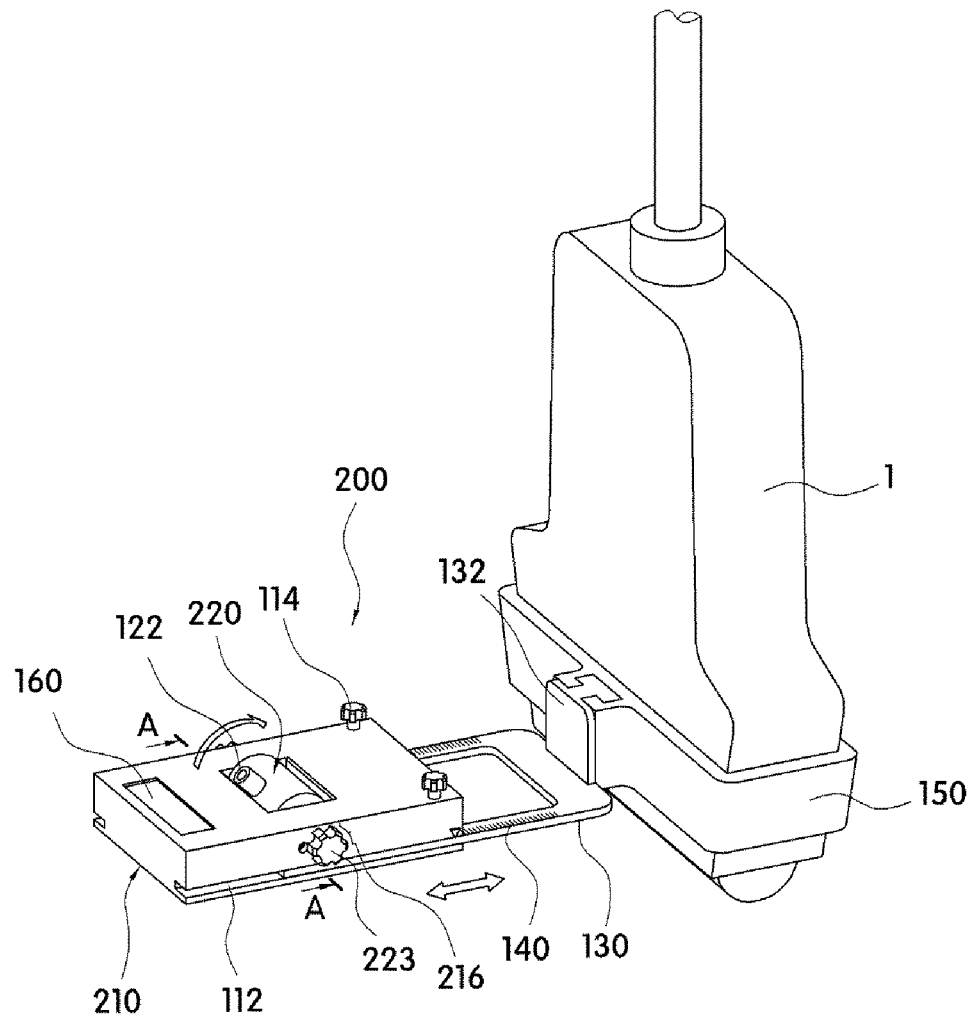
FIG. 7 is a perspective view illustrating a guide device for injection needle puncture according to another embodiment of the present invention.
Figure 8:
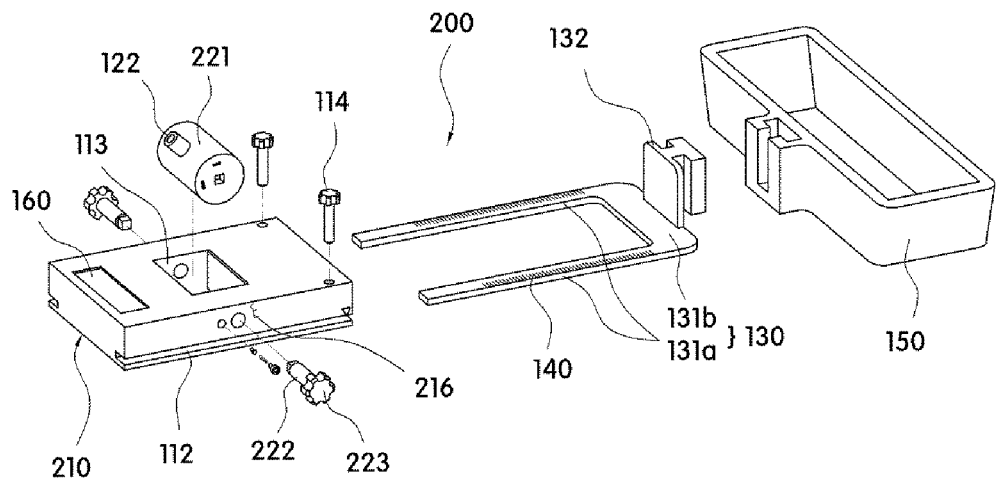
FIG. 8 is an exploded view of FIG. 7.
Figure 9:
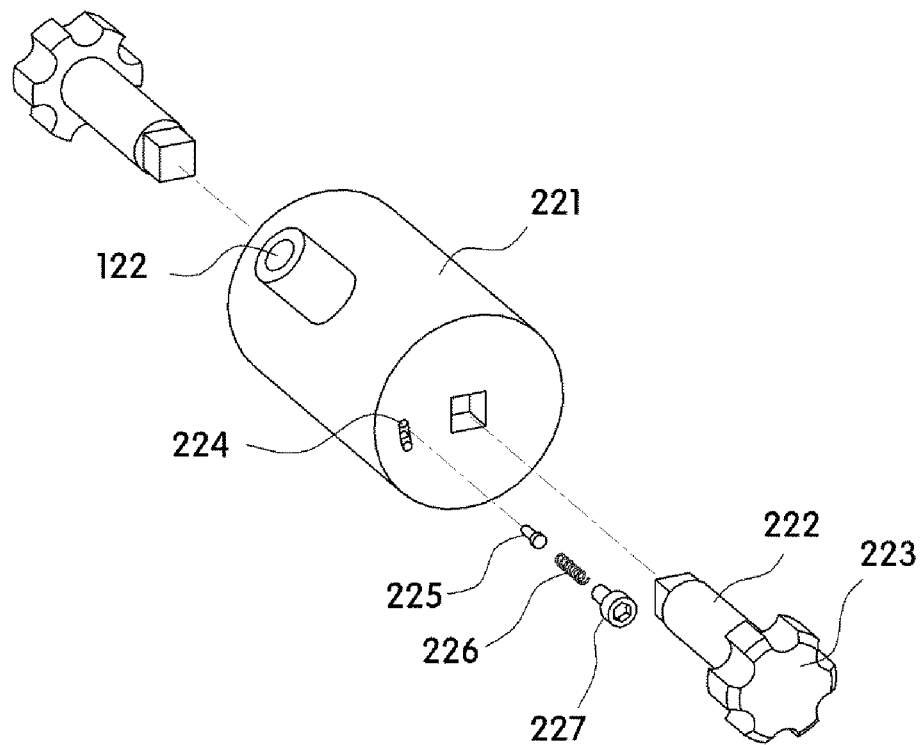
FIG. 9 is an exploded view illustrating a guide part in FIG. 7.

Further, although the guide hole 122 may be formed to have the same cross-sectional area throughout its entire length (see FIG. 6A), the guide hole 122 may also be formed to have a cross-sectional area that gradually decreases from top to bottom at least partially or entirely so that the injection needle 10 that has entered the guide hole 122 can easily enter and pass through a lower side (see FIGS. 6B and 6C).

That is, the guide hole 122 may be formed to have a cross-sectional area that gradually decreases from top to bottom throughout its entire length (see FIG. 6C) or may be formed to have a cross-sectional area that gradually decreases from top to bottom along only a part of its entire length (see FIG. 6B).

Meanwhile, when the cross-sectional area of the guide hole 122 gradually decreases as described above, the lower end side of the guide hole 122 through which the injection needle 10 passes maintains an initial angle of inclination.

Figure 2:
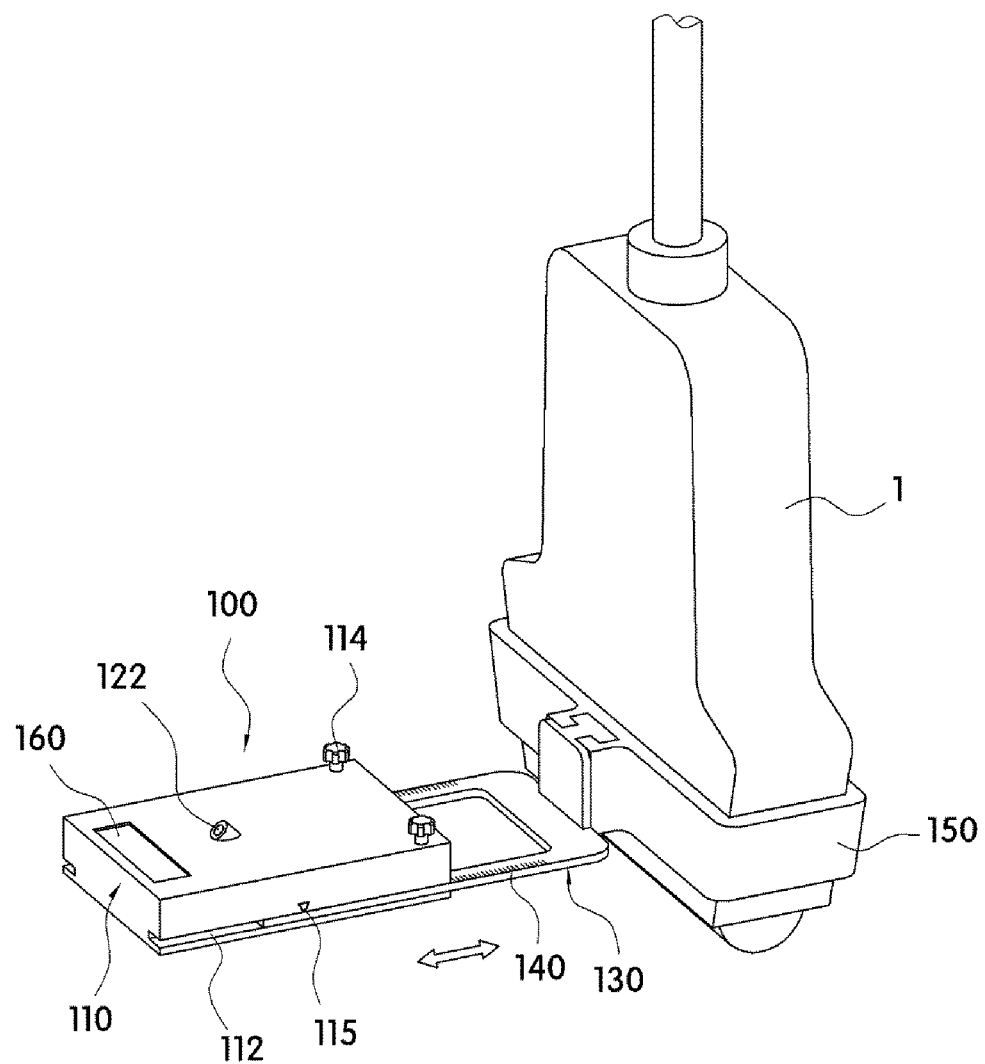
FIG. 2 is a perspective view illustrating a guide device for injection needle puncture according to an embodiment of the present invention.
Figure 3:
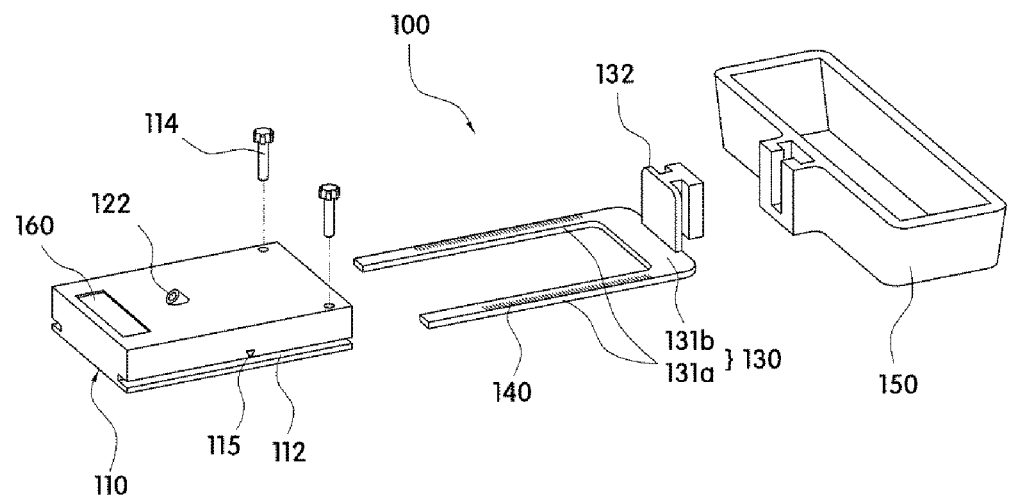
FIG. 3 is an exploded view of FIG. 2.

The guide part 120 may be integrally formed with the body 110 as illustrated in FIGS. 2 to 4.

That is, the guide hole 122 is formed to penetrate the body 110 along the height direction of the body 110 so that a separation distance between the guide hole 122 and one side of the medical ultrasound apparatus 1 can be adjusted by the guide hole 122 sliding together with the body 110 when the body 110 moves.

Also, the guide part 220 may be formed as a separate member from the body 210 as illustrated in FIGS. 7 to 11, and the set angle of the guide hole 122 may be adjusted by the guide part 220 being rotatably coupled to the body 210.

For this, the guide part 220 includes a guide main body 221 rotating about a hinge shaft 222 with respect to the body 210, and the guide hole 122 is formed to penetrate the guide main body 221 along a height direction of the guide main body 221.

When the guide part 220 is provided to be rotatable with respect to the body 210 as described above, a through-hole 113 configured to accommodate the guide part 220 is formed in the body 210 to penetrate the body 210 along the height direction of the body 210.

Further, a lever part 223 for allowing a user to rotate the hinge shaft 222 and adjust an angle of the guide main body 221 may be provided at an end of the hinge shaft 222. Accordingly, the user may adjust the set angle of the guide hole 122 to be any angle within the range of 0° to 90° by rotating the guide main body 221 with respect to the body 210 by using the lever part 223.

In this case, an angle indicating part 216 may be provided at one side of the body 210 to check an angle of rotation of the guide main body 221. In this way, the user can easily check a currently set angle of the guide main body 221 through the angle indicating part 216 and thus check the currently set angle of the guide main body 221 and change the guide main body 221 to be at a desired angle when the angle needs to be changed.

In this case, a plurality of angle adjustment grooves 224 are concentrically arranged about the hinge shaft 222 at one side of the guide main body 221, and a fixing pin 225 that is inserted through a side portion of the body 210 may be inserted into the angle adjustment grooves 224 to restrict rotation of the guide main body 221.

In this way, by changing the set angle of the guide main body 221 and the guide hole 122 and then restricting rotation of the guide main body 221 by using the fixing pin 225, the user allows the guide main body 221 and the guide hole 122 to be maintained at the changed angle.

Figure 11:
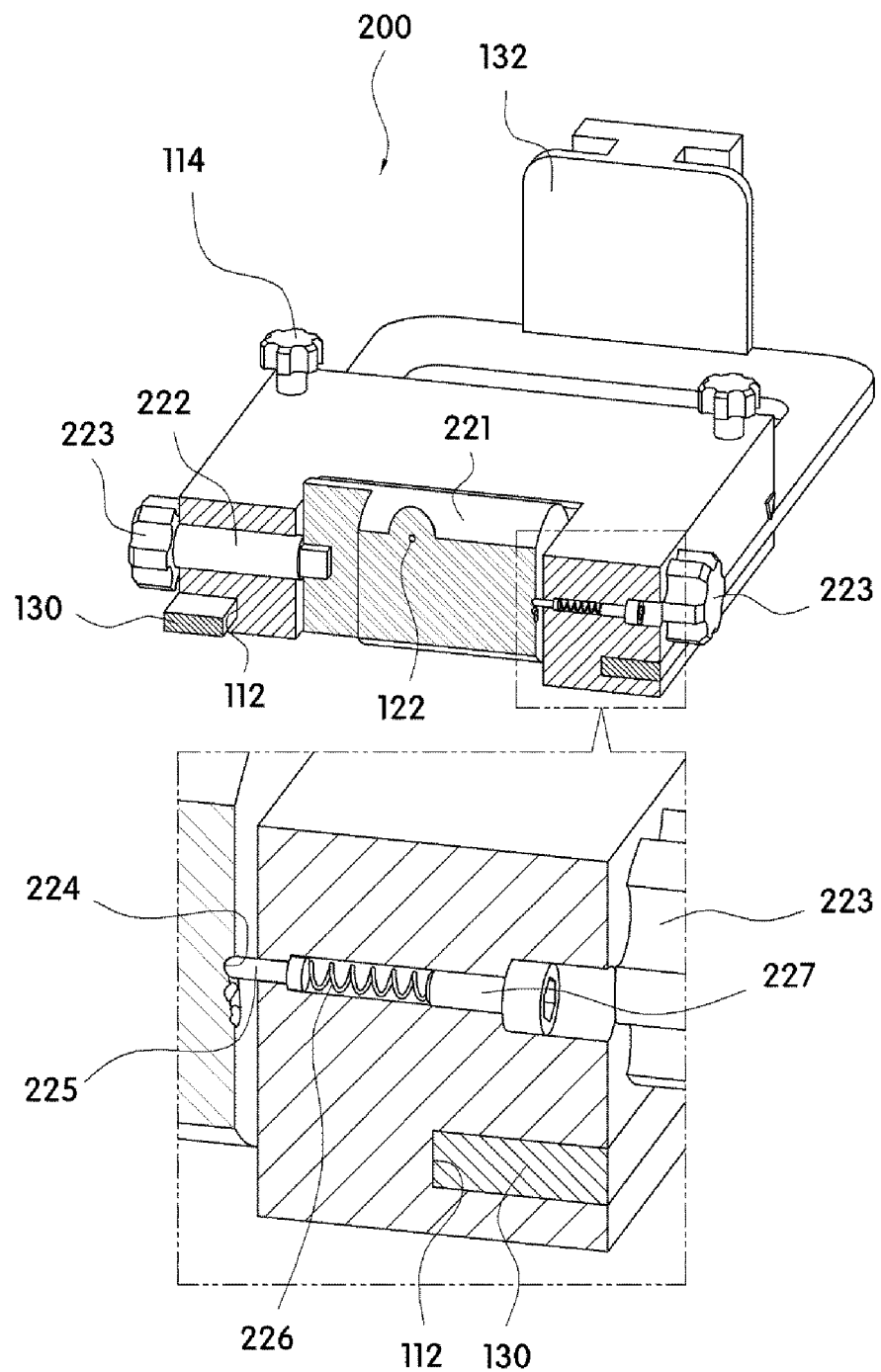
FIG. 11 is a cut-away view taken along line B-B in FIG. 7.

Further, as illustrated in FIG. 11, a spring member 226 configured to press the fixing pin 225 in one direction may be provided at an end side of the fixing pin 225. The spring member 226 is prevented from falling to the outside by a fixing screw 227 that is fixed and coupled to one side of the guide main body 221. In this way, the spring member 226 always presses the fixing pin 225 toward the guide main body 221.

Accordingly, an end of the fixing pin 225 always maintains a state of being inserted into the angle adjustment grooves 224 of the guide main body 221 and restricts rotation of the guide main body 221 with respect to the bodies 110 and 210.

Further, by the spring member 226 disposed at the end side of the fixing pin 225, when the guide main body 221 is rotated by the lever part 223, the fixing pin 225 retracts from the angle adjustment grooves 224 by the rotational force and compresses the spring member 226. In addition, when the end of the fixing pin 225 is placed at an adjacent angle adjustment groove 224, the fixing pin 225 advances by an elastic force stored in the spring member 226 and is inserted into the angle adjustment groove 224. In this way, the guide main body 221 is maintained at the changed angle.

By the guide part 220 provided to be rotatable with respect to the bodies 110 and 210 and the set angle of the guide hole 122 being adjustable as described above, even when the depth d2 from the skin to the target position is the same the separation distance between the medical ultrasound apparatus 1 and the guide hole 122 may be variously adjusted.

For example, although the separation distance between the guide hole 122 and the medical ultrasound apparatus 1 for inserting the injection needle 10 is the same as the depth d2 from the skin to the target position when the set angle of the guide hole 122 is 45°, the separation distance between the guide hole 122 and the medical ultrasound apparatus 1 for inserting the injection needle 10 is set to be $\sqrt{3}$ times the separation distance between the guide hole 122 and the medical ultrasound apparatus 1 in the case in which the set angle of the guide hole 122 is 45° when the set angle of the guide hole 122 is 30°.

Thus, when it is difficult for the injection needle 10 to be inserted at a position of puncture for inserting the injection needle 10 into skin, a position into which the injection needle will be inserted may be conveniently changed by changing the set angle of the guide hole 122 and changing the separation distance between the medical ultrasound apparatus 1 and the guide hole 122 into which the injection needle will be inserted.

The sliding member 130 is for allowing the separation distance between the medical ultrasound apparatus 1 and the guide hole 122 to be adjusted and is slidably coupled to the bodies 110 and 210.

That is, the sliding member 130 includes a pair of horizontal bars 131a having a predetermined length and a connecting bar 131b configured to connect the pair of horizontal bars 131a, and sliding of the sliding member 130 is guided by the groove part 112 by the pair of horizontal bars 131a being inserted into the groove part 112 of the bodies 110 and 210.

Also, a contact part 132 coming into contact with one surface of the medical ultrasound apparatus 1 is provided at a free end side of the sliding member 130.

In this case, the contact part 132 may be a plate-shaped member perpendicularly extending from an end of the sliding member 130 toward one side.

An end of the sliding member 130 comes into contact with one surface of the medical ultrasound apparatus 1 via the contact part 32 so that a reference point of the separation distance between the guide hole 122 and the medical ultrasound apparatus 1 is defined when the guide hole 122 is spaced apart from the medical ultrasound apparatus 1.

Here, although the contact part 132 is illustrated as coming into contact with one surface of the medical ultrasound apparatus 1 in the drawing, it should be noted that embodiments are not limited thereto, and the contact part 132 may also come into contact with the medical ultrasound apparatus 1 in the form of being locked to one side of the medical ultrasound apparatus 1.

Also, although the sliding member 130 is illustrated and described as being provided the pair of horizontal bars 131a and the connecting bar 131b, it should be noted that the embodiments are not limited thereto, and the sliding bar 130 may also be provided as a single bar.

Meanwhile, a fixing member 150 for fixing to the medical ultrasound apparatus 1 may be provided at an end side of the contact part 132. The fixing member 150 may be a hollow frame part to surround a perimeter of the medical ultrasound apparatus 1.

In this way, by the medical ultrasound apparatus 1 being inserted into the frame part and temporarily fixed, the user may grip the medical ultrasound apparatus 1 with one hand and freely slide the bodies 110 and 210 with the other hand.

Although the fixing member 150 may be integrally formed with the contact part 132, the fixing member 150 may also be detachably coupled to the contact part 132 so that, when the size of the medical ultrasound apparatus 1 is different, the fixing member 150 may be replaced with another fixing member that fits the medical ultrasound apparatus 1.

The guide devices for injection needle puncture 100 and 200 according to an embodiment of the present invention may include a scales part 140 to check the separation distance between the medical ultrasound apparatus 1 and the guide hole 122.

The scales part 140 may be provided along the longitudinal direction at one surface of the sliding member 130 or may be provided along the longitudinal direction at one surface of the bodies 110 and 210. In such cases, the scales part 140 may have the form of a ruler.

In another embodiment, a display part 160 for checking the separation distance between the medical ultrasound apparatus 1 and the guide hole 122 may be provided at one surface of the bodies 110 and 210.

The separation distance between the guide hole 122 and the medical ultrasound apparatus 1 may be displayed with letters, e.g., number, on the display part 160.

Here, the separation distance between the guide hole 122 and the medical ultrasound apparatus 1 that is displayed on the display part 160 may be a distance that matches and is in 1:1 ratio with the vertical depth d2 of the injection needle that needs to be inserted into the human body through the guide hole 122.

For this, a converting part (not illustrated) configured to convert the angle of inclination of the guide hole 122 and the separation distance between the guide hole 122 and the medical ultrasound apparatus 1 may be provided at an inside of the bodies 110 and 210 so that a distance that matches and is in 1:1 ratio with the vertical depth d2 of the injection needle that needs to be inserted into the human body through the guide hole 122 can be displayed.

Accordingly, even when the guide hole 122 is provided to have any angle between 0° to 90° as the set angle, a distance that matches and is in 1:1 ratio with a distance from the skin to a target position is always displayed on the display part 160 by the converting part. Thus, without requiring the separation distance between the guide hole 122 and the medical ultrasound apparatus 1 to be calculated according to the set angle of the guide hole 122, the user may set a precise spaced-apart position of the guide hole 122 by sliding the bodies 110 and 210 so that the number displayed on the display part 160 matches the distance d2 from the skin to the target position.

Here, the converting part is electrically connected to a sensor provided at one side of the sliding member 130 or the bodies 110 and 210 to calculate a converted number that will be output on the display part 160 on the basis of a sliding distance of the sliding member 130 or the bodies 110 and 210.

Because the converting method is a known art, the detailed description thereof will be omitted.

Although a digital method in which a distance measured by the sensor is converted by the converting part as the number output on the display part 160 has been exemplified, embodiments are not limited thereto, and the distance may also be converted using an analog method.

Further, it should be noted that a relative movement distance of the bodies or the sliding member that slide depending on the set angle of the guide hole 122 can be increased or decreased by a known mechanical method such as gear coupling.

Also, it should be noted that the guide devices for injection needle puncture 100 and 200 according to an embodiment of the present invention may simultaneously include both a ruler and a display part configured to check the separation distance between the medical ultrasound apparatus 1 and the guide hole 122, more particularly, a separation distance between a lower end of the guide hole 122 and the medical ultrasound apparatus 1, or may include only one of them.

Further, a separate display 115 may be provided at a position at one side of the bodies 110 and 120 corresponding to the lower end of the guide hole 122 so that a precise position of the lower end of the guide hole 122 that is formed to be inclined at a predetermined angle can be easily checked in a process in which the user checks a separation distance d1 between the medical ultrasound apparatus 1 and the guide hole 122.

Although embodiments of the present invention have been described above, the spirit of the present invention is not limited to the embodiments proposed herein, and although one of ordinary skill in the art who understands the spirit of the present invention should be able to easily propose other embodiments within the scope of the same spirit by addition, modification, omission, etc. of elements, these embodiments should also be construed as belonging to the scope of the spirit of the present invention.

The invention claimed is:

1. A guide device for injection needle puncture, the guide device comprising:
a body;
a guide part that has a guide hole provided therein to be tilted at a certain angle along a height direction, the guide hole allowing an injection needle to pass therethrough so that, when the injection needle is punctured into a human body, an insertion angle of the insertion needle is guided and the insertion angle is constantly maintained; and
a sliding member slidably coupled to the body,
wherein a separation distance between a medical ultrasound apparatus and the guide hole is adjusted so that a target position into which an end of the injection needle is to be inserted is located on an entry path of the injection needle by relative movement of the body or the sliding member,
wherein the guide part includes a guide main body rotating about a hinge shaft with respect to the body to adjust an angle of the guide hole, and the guide hole is formed to penetrate the guide main body along a height direction of the guide main body,
wherein a plurality of angle adjustment grooves that are concentrically arranged about the hinge shaft are provided at one side of the guide main body, and a fixing pin that is inserted through a side portion of the body is inserted into the angle adjustment grooves to fix the angle of rotation of the guide main body.

2. The guide device of claim 1, wherein a partial length of the guide hole including an upper end exposed to the outside is formed to have a cross-sectional area that is relatively larger than a remaining portion so that insertion of the injection needle into the guide hole is facilitated.

3. The guide device of claim 1, wherein a cross-sectional area of the guide hole gradually decreases from top to bottom at least partially or entirely so that insertion of the injection needle into the guide hole is facilitated.

4. The guide device of claim 1, further comprising a scales part to check the separation distance between the medical ultrasound apparatus and the guide hole.

5. The guide device of claim 4, wherein the scales part has the form of a ruler provided along a longitudinal direction at one surface of the sliding member.

6. The guide device of claim 4, wherein the scales part has the form of a ruler provided along a longitudinal direction at one surface of the body.

7. The guide device of claim 4, wherein an indicator configured to indicate a position corresponding to a lower end of the guide hole is provided at one side of the body.

8. The guide device of claim 1, wherein the guide hole is formed to penetrate the body along the height direction of the body.

9. The guide device of claim 1, wherein a lever part is provided at one end of the hinge shaft.

10. The guide device of claim 1, wherein an angle indicating part is provided at one side of the body to check an angle of rotation of the guide main body.

11. The guide device of claim 1, wherein the separation distance between the guide hole and the medical ultrasound apparatus is a linear distance between the lower end of the guide hole and a lower end of the medical ultrasound apparatus.

12. The guide device of claim 1, wherein an angle of inclination of the guide hole is formed to be an angle in the range of 0° to 90° with respect to a horizontal surface.

13. The guide device of claim 12, wherein the angle of inclination of the guide hole is formed to be any one angle of 30°, 45°, or 60° with respect to the horizontal surface.

14. The guide device of claim 1, wherein a contact part coming into contact with one surface of the medical ultrasound apparatus is provided at a free end side of the sliding member.

15. The guide device of claim 14, wherein the contact part is a plate-shaped member perpendicularly extending from an end of the sliding member toward one side.

16. The guide device of claim 1, wherein a stopper member configured to restrict movement of the sliding member is provided in the body.

17. The guide device of claim 16, wherein the stopper member is at least one set screw that is screw-coupled to one side of the body, and when the set screw moves by rotation, an end of the set screw presses the sliding member at the middle of the length thereof.

* * * * *